(12) United States Patent
Hinek et al.

(10) Patent No.: US 8,470,774 B2
(45) Date of Patent: Jun. 25, 2013

(54) DEOXYCORTICOSTERONE INDUCED ELASTIN PRODUCTION

(75) Inventors: Aleksander Hinek, Toronto (CA); Thomas F. Mitts, Visalia, CA (US)

(73) Assignees: Human Matrix Sciences, LLC, Visalia, CA (US); The Hospital for Sick Children, Toronto, Ontario (CA)

( * ) Notice: Subject to any disclaimer, the term of this patent is extended or adjusted under 35 U.S.C. 154(b) by 0 days.

(21) Appl. No.: 13/405,744

(22) Filed: Feb. 27, 2012

(65) Prior Publication Data

US 2012/0195914 A1    Aug. 2, 2012

Related U.S. Application Data

(63) Continuation of application No. 12/157,141, filed on Jun. 6, 2008, now Pat. No. 8,148,327.

(60) Provisional application No. 60/942,305, filed on Jun. 6, 2007.

(51) Int. Cl.
*A61K 38/16* (2006.01)
*A61K 38/22* (2006.01)
*A61K 38/39* (2006.01)
*A61K 39/395* (2006.01)
*A61K 31/33* (2006.01)
*A61K 31/365* (2006.01)
*C07K 16/26* (2006.01)
*C07J 17/00* (2006.01)
*C07J 21/00* (2006.01)

(52) U.S. Cl.
USPC .......... 514/9.7; 514/17.2; 514/18.6; 514/462; 424/198.1; 424/130.1; 530/399; 530/387.1; 540/41; 540/102; 540/325

(58) Field of Classification Search
None
See application file for complete search history.

(56) References Cited

U.S. PATENT DOCUMENTS

| | | | |
|---|---|---|---|
| 4,543,351 A | 9/1985 | Messina | |
| 5,885,974 A | 3/1999 | Danielov | |
| 6,303,588 B1 | 10/2001 | Danielov | |
| 2007/0275938 A1 | 11/2007 | Reading et al. | |
| 2011/0165176 A1 | 7/2011 | Hinek et al. | |

FOREIGN PATENT DOCUMENTS

| | | |
|---|---|---|
| DE | 2401446 A1 | 7/1974 |
| FR | 2213776 A1 | 9/1974 |
| JP | 60028927 A | 2/1985 |
| WO | WO 96/17621 A | 6/1996 |
| WO | WO 97/42970 A1 | 11/1997 |

OTHER PUBLICATIONS

Fardella et al. Molecular Biol Mineralocorticoid metabolism. Annu Rev Nutr 16: 443-470, 1996.*

Funder, J.W. Minireview: aldosterone and mineralocorticoid receptors: past, present, and future. Endocrinology 151: 5098-5102, 2010.*

Sharp et al. Mechanism of action of aldosterone. Physiol Rev 46(4): 593-633, 1966.*

Vinson, G.P. The mislabelling of deoxycorticosterone: making sense of corticosteroid structure and function. J Endocrinol 211: 3-16, 2011.*

Chai et al. "Genomic and nongenomic effects of aldosterone in the rat heart: why is spironolactone cardioprotective?" 2005, *Br. J. of Pharmacol.* 145:664-671.

He et al. "Oxidation of CaMKII determines the cardiotoxic effects of aldosterone" Dec. 2011, *Nature Medicine* 17(12):1610-1691.

Li et al. "Elastin Overexpression by Cell-based Gene Therapy Preserves Matrix and Prevents Cardiac Dilation" Mar. 21, 2012, *J. Cell Mol. Med.* [epub ahead of print].

Mizuno et al. "Elastin Stabilizes an Infarct and Preserves Ventricular Function" 2005, *Circulation* 112(1):I-81-I-88.

Banker et al. "Modern Pharmaceutics" 1979, Marcel Dekker, Inc., New York (TOC).

Bunda et al. "Aldosterone Induces Elastin Production in Cardiac Fibroblasts through Activation of Insulin-Like Growth Factor-I Receptors in a Mineralocorticoid Receptor-Independent Manner" 2007, *Am. J. Path.* 171:809-819.

Bunda et al. "Aldosterone Stimulates Elastogenesis in Cardiac Fibroblasts Via Mineralocorticoid Receptor-Independent Action Involving The Consecutive Activation of Gα13, c-Src, The Insulin-Like Growth Factor-I Receptor, and Phosphatidylinositol 3-Kinase/Akt" Jun. 12, 2009, *Journal of Biological Chemistry* 284(24):16633-16647.

Clayman "Contact Dermatitis Treated with Fludrocortisone: Steroid-Antibiotic Combination in the Inflammatory Dermatoses" 1958, *J. Med. Soc. New Jersey* 55(4):168-169.

Goodman et al. "The Pharmaceutical Basis of Therapeutics, 6th ed." 1980, MacMillan Publishing Co., New York (TOC).

Hinek et al. "Decreased elastin deposition and high proliferation of fibroblasts from Costello syndrome are related to functional deficiency in the 67-kD elastin-binding protein" 2000, *Am. J. Genet.* 66(3):859-872.

Hinek et al. "Impaired Elastic-Fiber Assembly by Fibroblasts from Patients with Either Morquio B Disease or Infantile GM1-Gangliosidosis Is Linked to Deficiency in the 67-kD Spliced Variant of β-Galactosidase" 2000, *Am. Hum. Genet.* 67(1):23-36.

Hinek et al. "Impaired elastogenesis in Hurler disease: dermatan sulfate accumulation linked to deficiency in elastin-binding protein and elastic fiber assembly" 2000, *Am. J. Pathol.* 156(3):925-938.

Hinek et al. "Proteolytic digest derived from bovine Ligamentum Nuchae stimulates deposition of new elastin-enriched matrix in cultures and transplants of human dermal fibroblasts" 2005, *Dermatol. Sci.* 39(3):155-166.

(Continued)

*Primary Examiner* — Bridget E Bunner
(74) *Attorney, Agent, or Firm* — Pepper Hamilton LLP

(57) ABSTRACT

Compositions and methods for inducing the deposition of elastin in skin by administering compositions including a mineralocorticoid, such as, for example, aldosterone and, optionally, a secondary active agent for enhancing or modulating the effect of the mineralocorticoid are described herein.

5 Claims, 11 Drawing Sheets
(9 of 11 Drawing Sheet(s) Filed in Color)

OTHER PUBLICATIONS

Mitts et al. "Aldosterone and Mineralocorticoid Receptor Antagonists Modulate Elastin and Collagen Deposition in Human Skin" Jun. 10, 2010, *Journal of Investigative Dermatology* advance online publication doi: 10.1038/jid.2010.155.

Rosenbloom et al. "Extracellular matrix 4: The elastic fiber" 1993, *FASEB J.* 7:1208-1218.

Ventura et al. "Effect of Chronic Oral Administration of a Low Dose of Captopril on Sodium Appetite of Hypothyroid Rats. Influence of Aldosterone" 2001, Treatment, *Braz J Med Biol Res* 34(3):407-411.

* cited by examiner

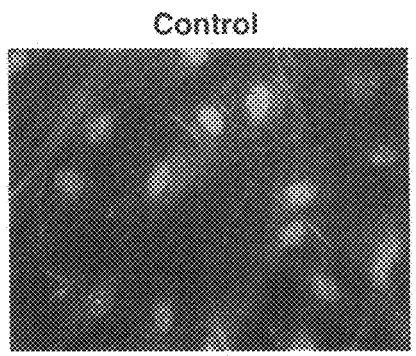
Fig. 2A — Control
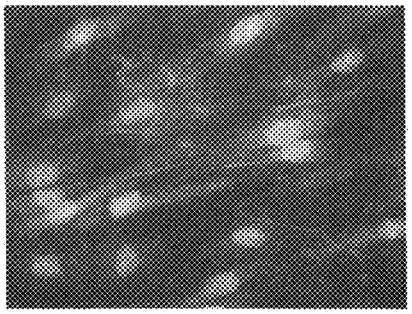
Fig. 2E — Spiro 2 μM
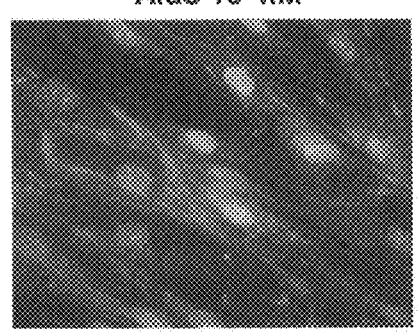
Fig. 2B — Aldo 10 nM
Fig. 2F — Aldo 10 nM + Spiro 2 μM
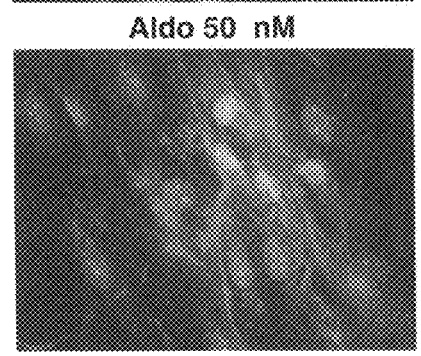
Fig. 2C — Aldo 50 nM
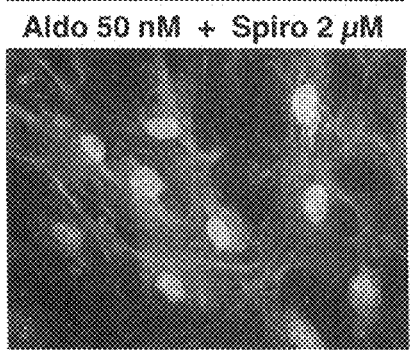
Fig. 2G — Aldo 50 nM + Spiro 2 μM
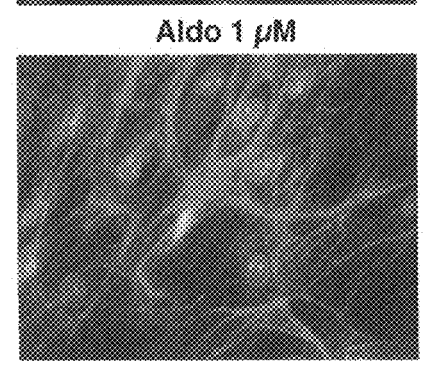
Fig. 2D — Aldo 1 μM
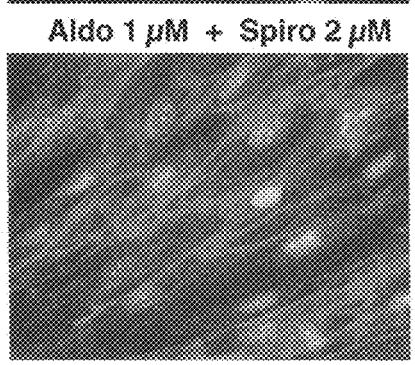
Fig. 2H — Aldo 1 μM + Spiro 2 μM

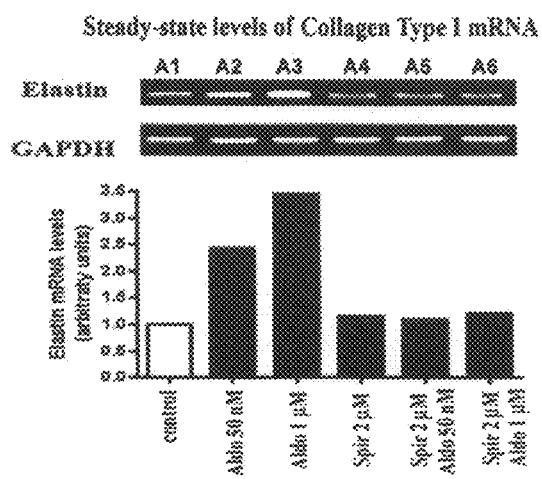
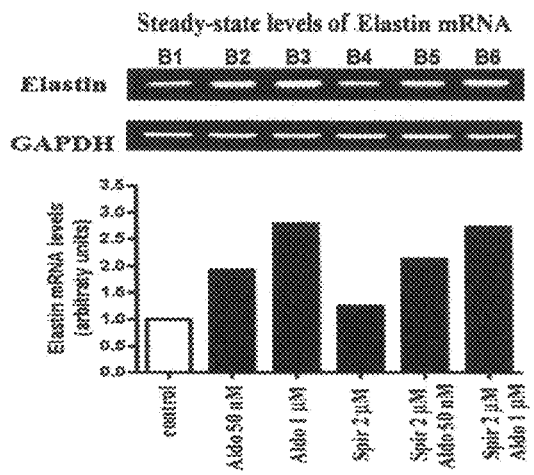
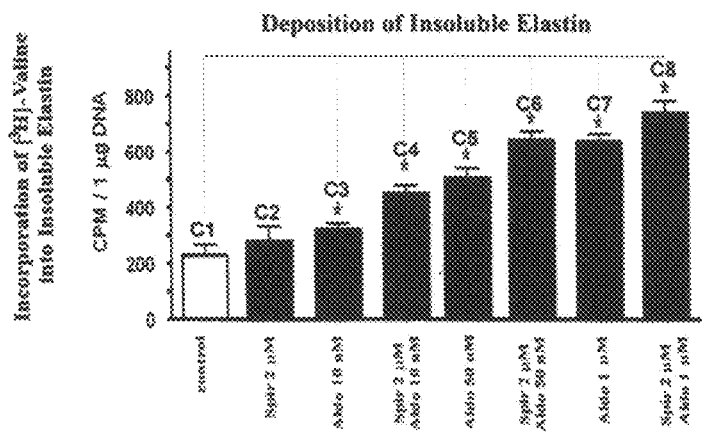
Fig. 3

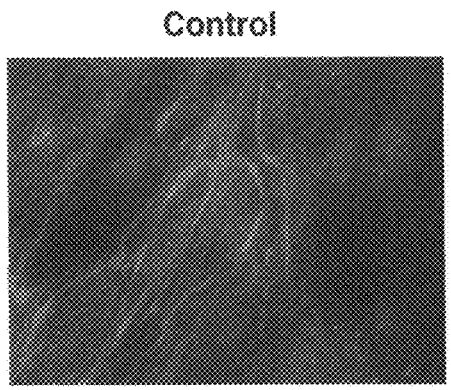
Fig. 4A — Control
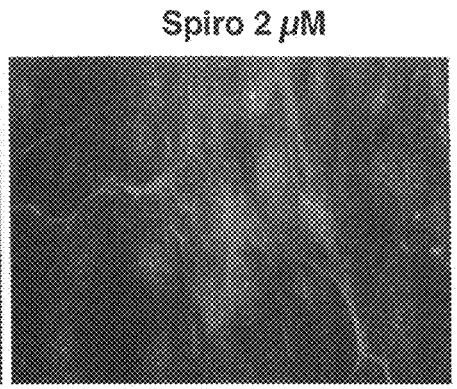
Fig. 4C — Spiro 2 μM
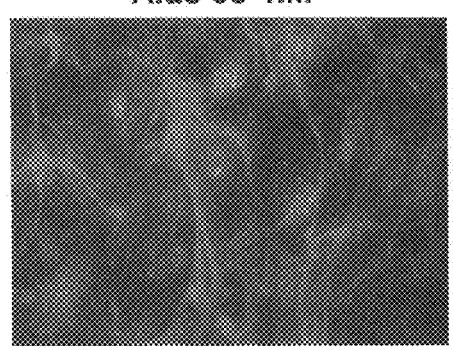
Fig. 4B — Aldo 50 nM
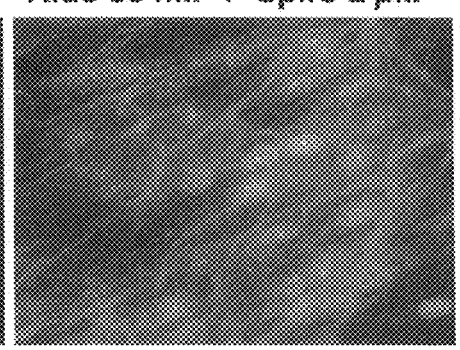
Fig. 4D — Aldo 50 nM + Spiro 2 μM
Deposition of Insoluble Elastin
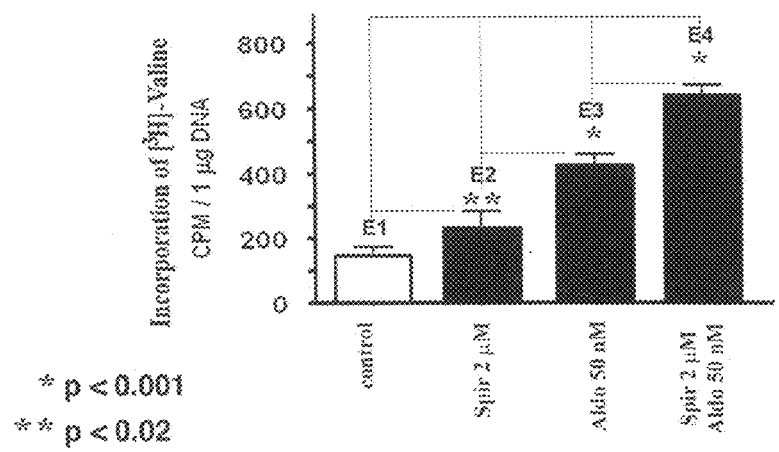
Fig. 4E
\* $p < 0.001$
\*\* $p < 0.02$

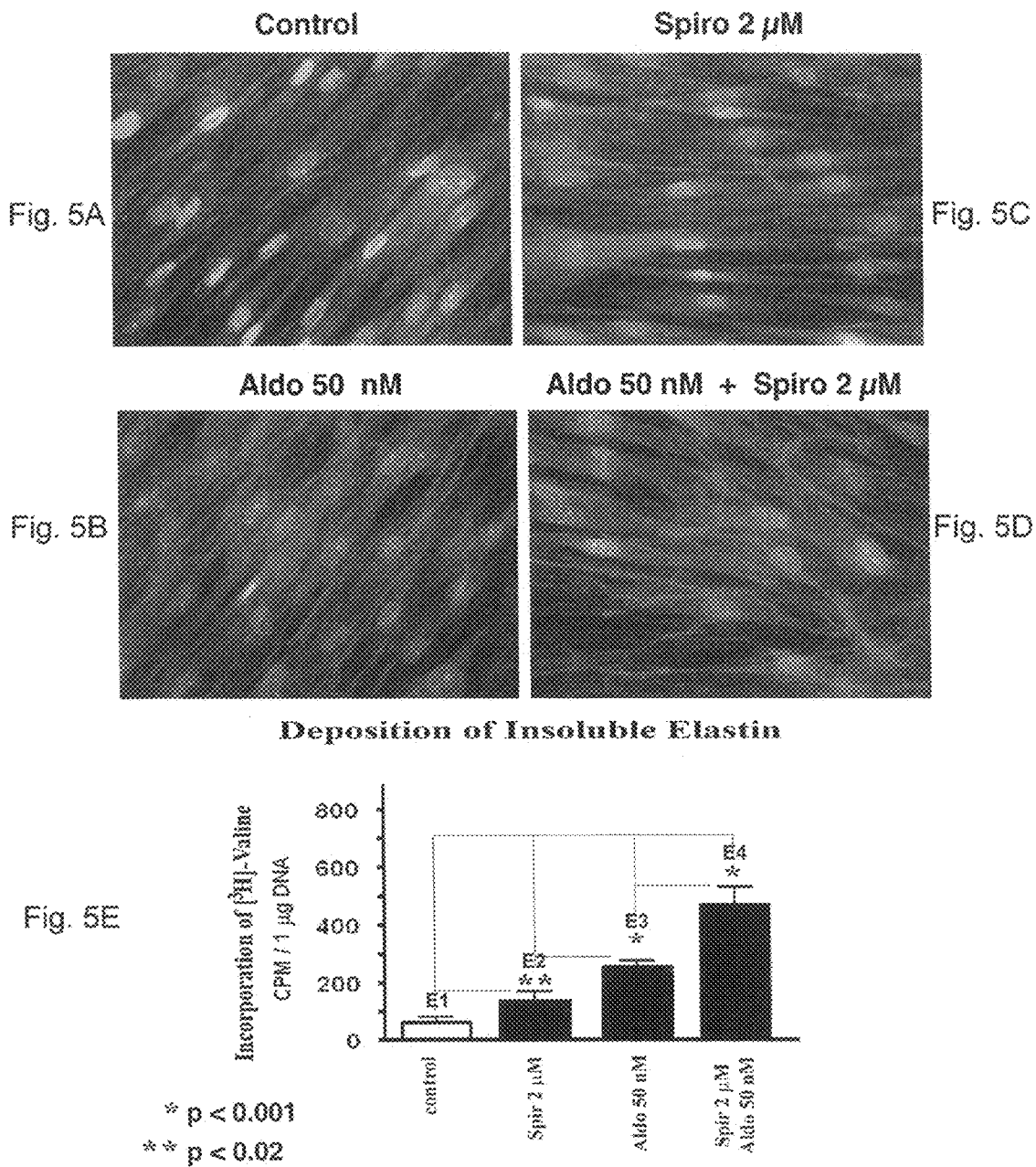

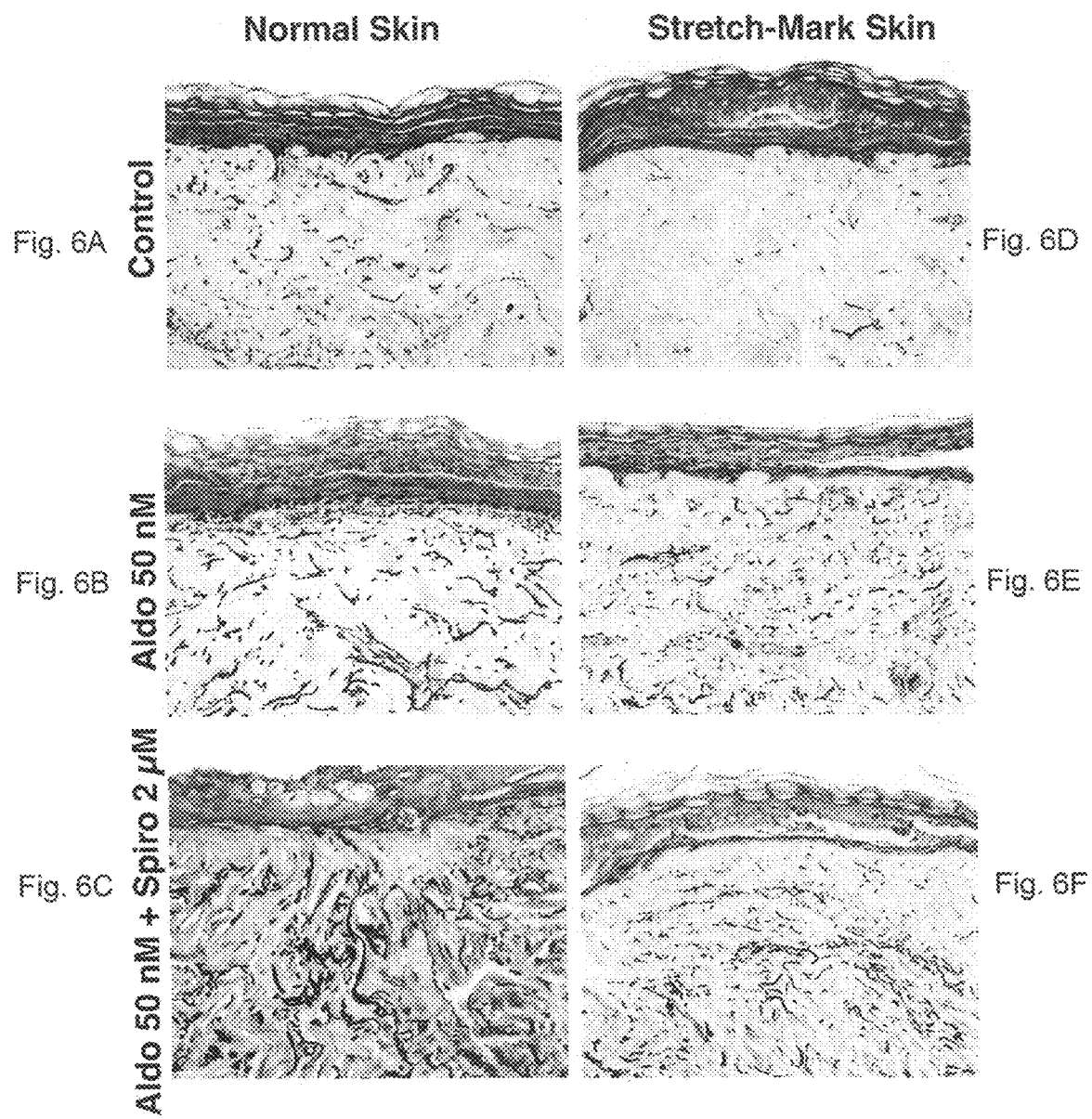

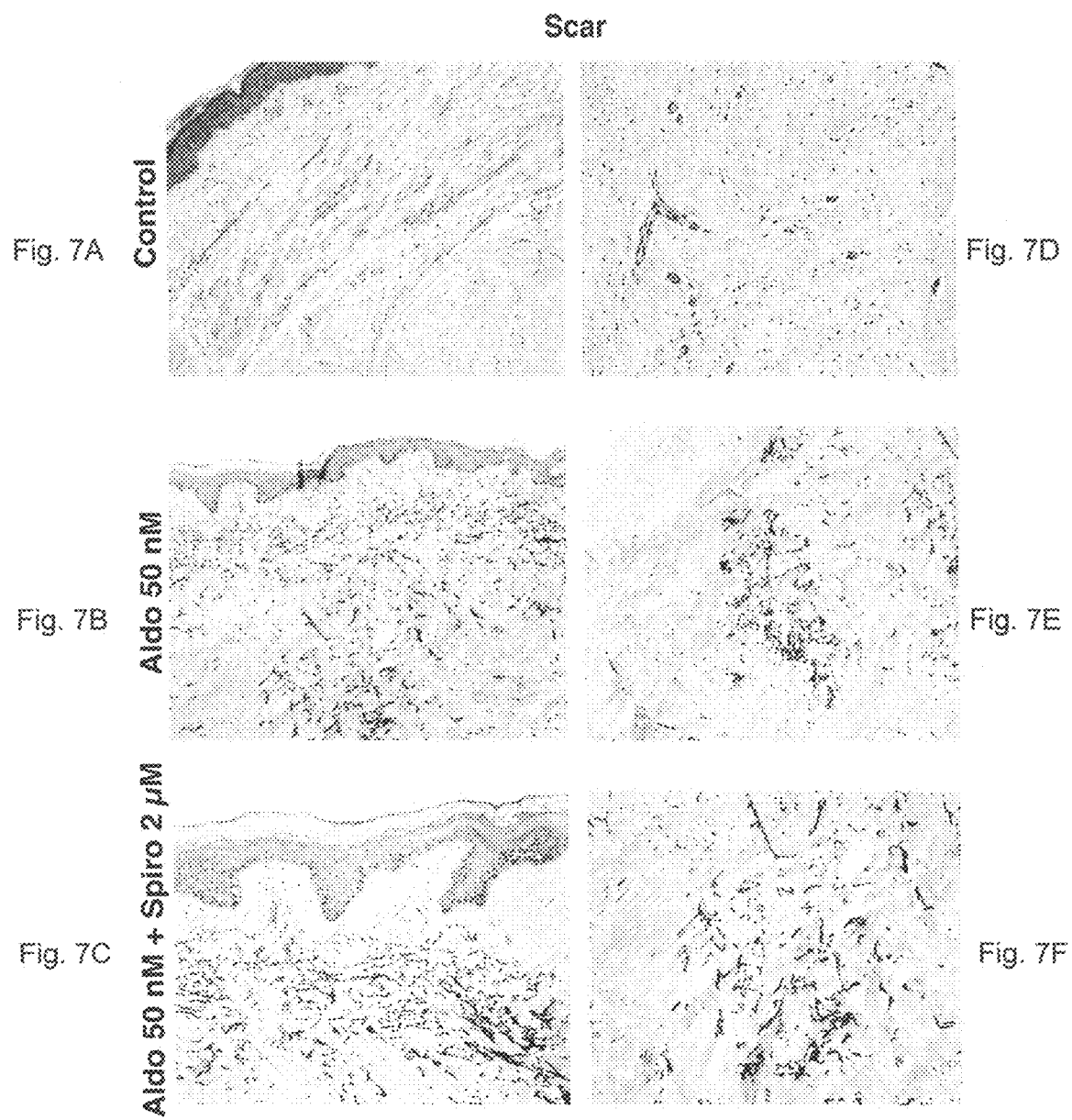

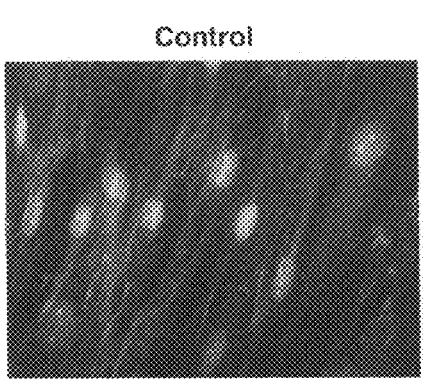
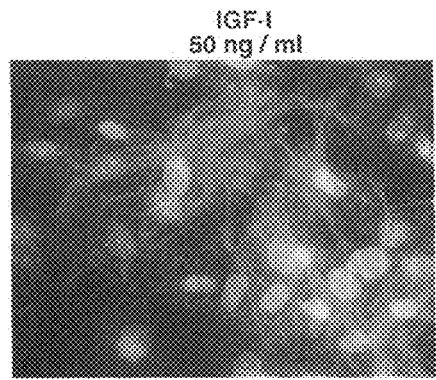
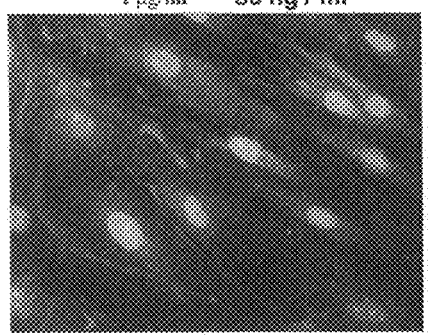
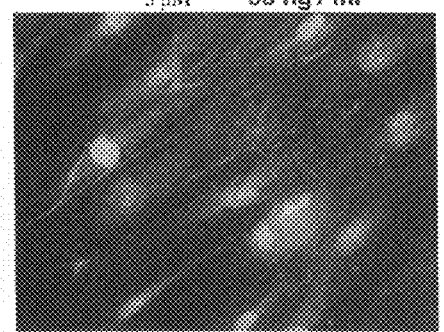
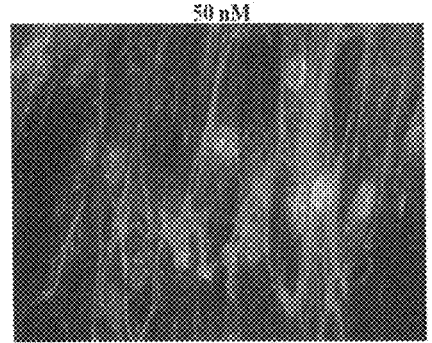
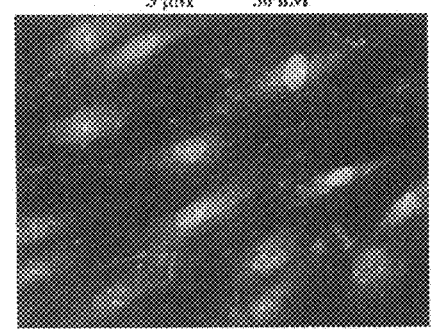
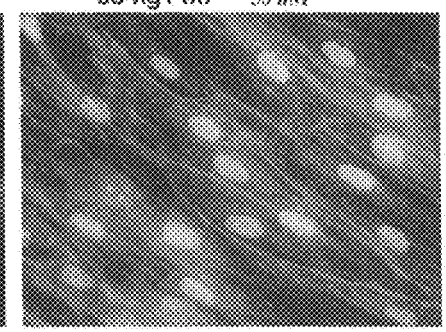
Fig. 8A  Fig. 8E  Fig. 8B  Fig. 8F  Fig. 8C  Fig. 8G  Fig. 8D  Fig. 8H

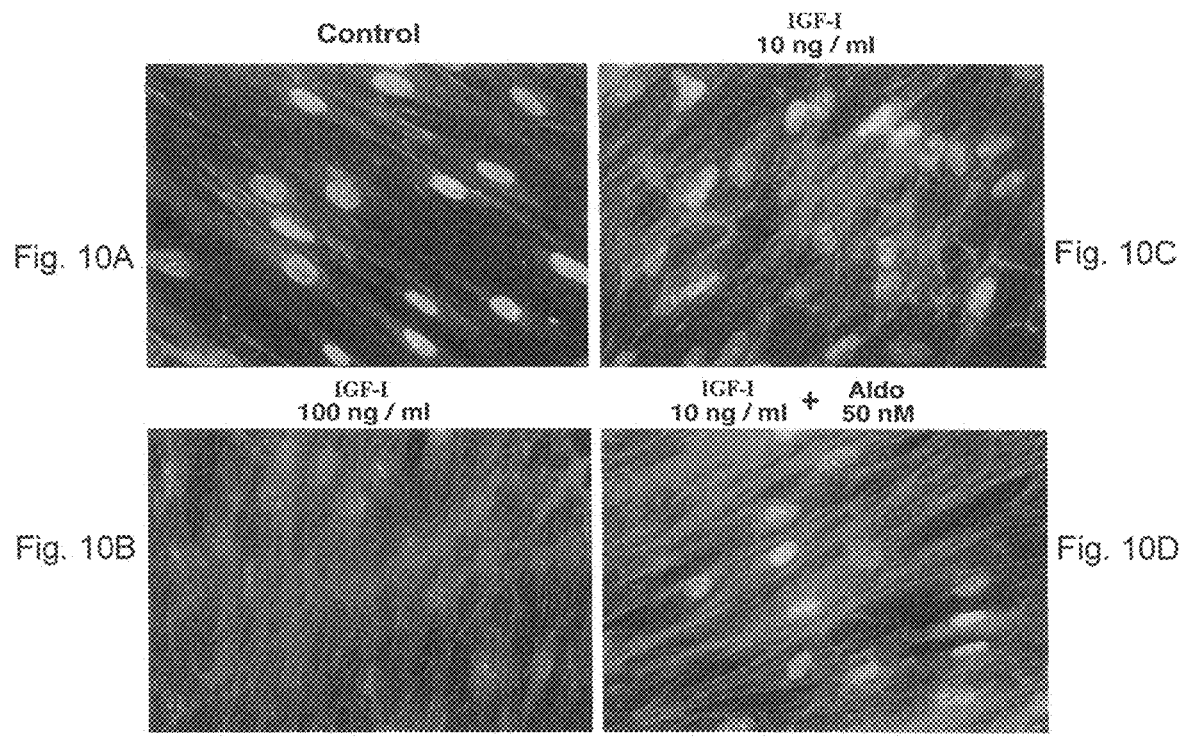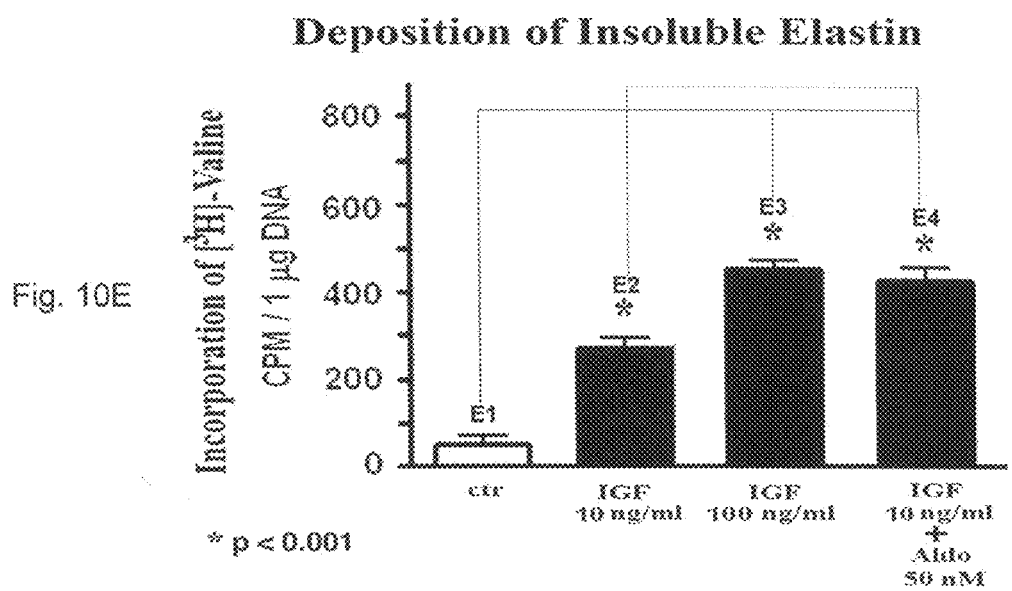

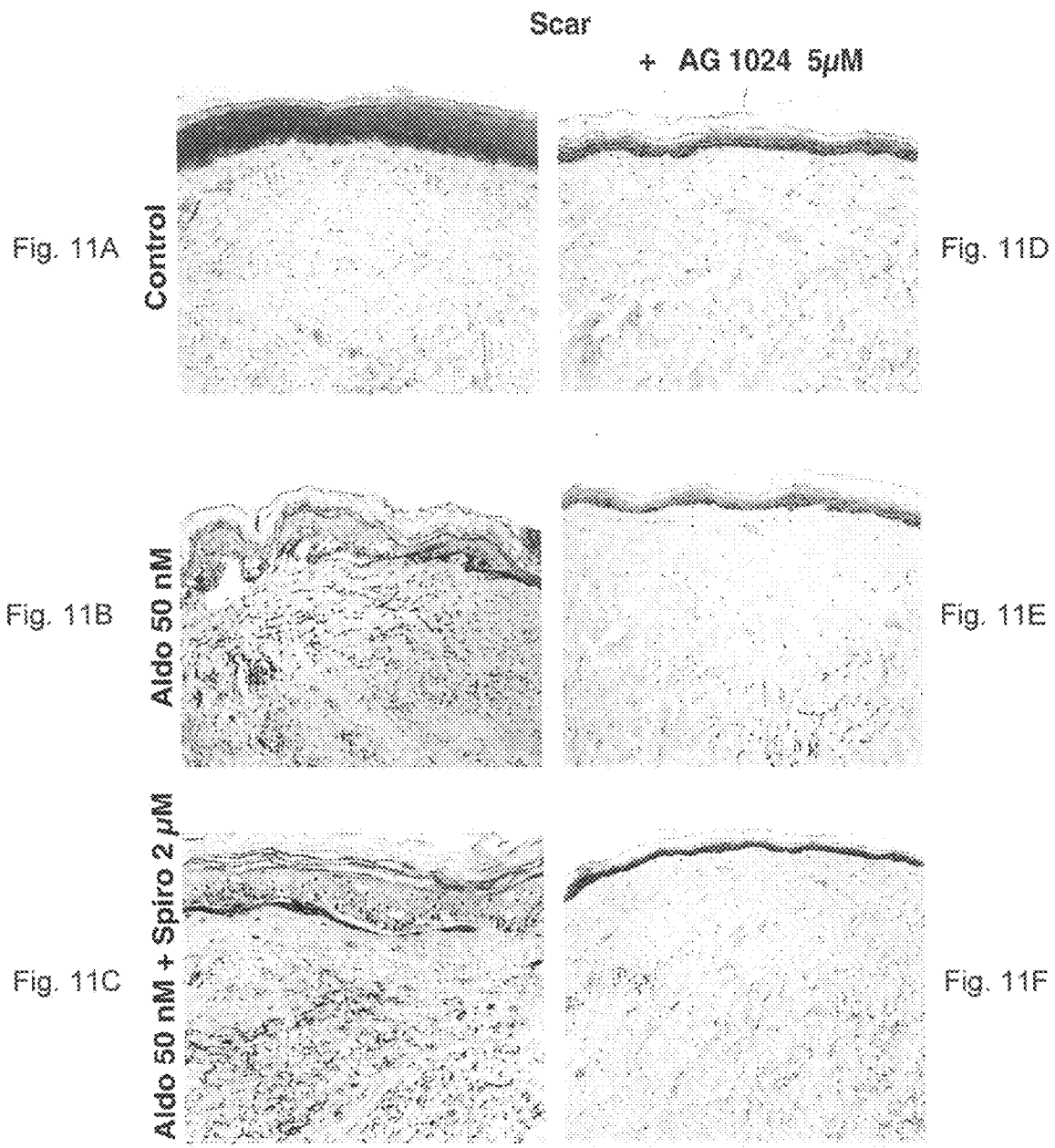

DEOXYCORTICOSTERONE INDUCED ELASTIN PRODUCTION

CROSS-REFERENCE TO RELATED APPLICATIONS

This is application is a continuation application of U.S. application Ser. No. 12/157,141, filed Jun. 6, 2008, now U.S. Pat. No. 8,148,327, which claims the benefit of U.S. Provisional Application No. 60/942,305, filed Jun. 6, 2007, each of which are incorporated herein by reference in its entirety.

BACKGROUND

The extracellular matrix (ECM) is made up of fibronectin, laminin, collagen and elastic fibers, as well as numerous glycosaminoglycans and protoglycans. These ECM components are organized into a network of rope-like structures which underlie many tissues, such as, blood vessels, skin, tendons, ligaments, and lungs. Of these ECM components, elastin is unique in that it can be stretched to over 150 percent of its original length and rapidly returns to its original size and shape. This property provides tissues in which elastin is incorporated with the ability to resume their original form after stretching. Therefore, elastin and elastin fibers allow these tissues to maintain the resiliency, stretchability and shape of these tissues.

Elastic fiber formation (elastogenesis) is a complex process involving intracellular and extracellular events. Cells such as fibroblasts, endothelial cells, chondroblasts or vascular smooth muscle cells, first synthesize and secrete glycoproteins that form a microfibrillilar scaffold into the extracellular space. Tropoelastin, the soluble precursor peptide of elastin, is synthesized in these cells by ribosomes in the rough endoplasmatic reticulum and transported through the Golgi apparatus and secretory vesicles that deposit tropoelastin in the extracellular space. Once outside the cell, tropoelastin is assembled into long chains and covalently cross-linked by lysyl oxidase. During crosslinking, unique composite amino acids, desmosine and isodesmosine, which join the tropoelastin chains, are formed and insoluble elastin is created.

Elastin fibers are composed of two major components: an amorphous, elastin core which makes up the bulk (>90%) of the fiber; and the 10-12 nm microfibrilary component surrounding the elastin core made up of glycoproteins, such as, for example, fibrillins, fibulins and microfibril-associated glycoproteins (MAGPs). Elastin may also be interwoven with non-elastic collagen fibers to limit stretching and prevent tearing of certain tissues. Mature (insoluble) elastin is metabolically inert and remains the most durable element of extracellular matrix. In undisturbed tissues, mature elastin may last for the lifetime of the tissue.

Deposition of elastin in the ECM appears to be controlled on both the transcriptional level (tropoelastin mRNA message expression) and post-transcriptional level (tropoelastin message stability). Other post-transcriptional events which control secretion of tropoelastin monomers, extracellular assembly of tropoelastin, and regulation of cross-linking of tropoelastin may also control elastin deposition.

Human skin is made up of two layers: a superficial layer, the epidermis, consisting of epithelial tissue and a deeper layer, the dermis, primarily composed of connective tissue. Together these layers form skin of thickness from less than about 0.5 mm up to 3 mm or even 4 mm. The dermis is essentially ECM of the skin and mechanically supports the cells and blood vessels of the epidermis and modulates the hydration of the skin.

Primary elastinopathies have been directly linked to alterations in the elastin gene including supravalvular aortic stenosis (SVAS), Williams-Beuren syndrome (WBS), Cutis Laxa, and a number of secondary elastinopathies which are caused by functional imbalance of other structural and auxiliary factors regulating elastic fiber deposition which has also been described including, for example, Marfan disease, GM-1-gangliosidosis, Morquio B, Hurler disease, Costello syndrome, Ehlers Danlos syndrome, and pseudoxanthoma elasticum (PXE). In the skin, a lack of elastin or genetic abnormalities affecting elastic fiber deposition lead to premature aging, most noticeably characterized by wrinkling and folding of the skin in children (pre-teenage) suffering from, for example, Costello Syndrome, Cutis Laxa and Pseudoxanthoma Elasticum. However, these conditions only affect elastic fibers in skin. Therefore, there is a high probability that development of wrinkles due to aging is caused by damage to or loss of elastic fibers in skin. Unfortunately, dermal fibroblasts lose their ability to make elastin by the end of puberty, and adult dermal fibroblasts cannot repair or replace damaged elastic fibers in skin leading to the irreversible formation of wrinkles.

BRIEF SUMMARY

Embodiments presented herein include a composition for treatment of skin including a mineralocorticoid and a secondary active agent selected from agents that reduce the net deposition of collagen in treated skin and agents that increase the expression or sensitivity of insulin growth factor receptor I.

Various embodiments include a pharmaceutical composition including a mineralocorticoid in an amount sufficient to improve skin when administered to a subject in need thereof and a pharmaceutically acceptable excipient.

Various other embodiments include a method for increasing the net deposition of elastin in skin including the step of administering an effective amount of a mineralocorticoid to a subject in need thereof.

Still other embodiments include a method for improving skin including the step of administering a pharmaceutical composition at least including an effective amount of a mineralocorticoid and a pharmaceutically acceptable excipient to a subject in need thereof.

DESCRIPTION OF DRAWINGS

The file of this patent contains at least one photograph or drawing executed in color. Copies of this patent with color drawing(s) or photograph(s) will be provided by the Patent and Trademark Office upon request and payment of the necessary fee.

For a fuller understanding of the nature and advantages of the present invention, reference should be made to the following detailed description taken in connection with the accompanying drawings, in which:

FIG. 2 shows representative micrographs (×400) of 7-day-old cultures of normal skin immuno-stained for elastin using green fluorescein-labeled anti-elastin antibody and nuclei stained using red propidium iodide that are untreated (A), treated with 10 nM aldosterone (Aldo) (B), 50 nM Aldo (C), 1 µM Aldo (D), 2 µM spironolactone (E), 10 nM Aldo and 2

Figure 1:
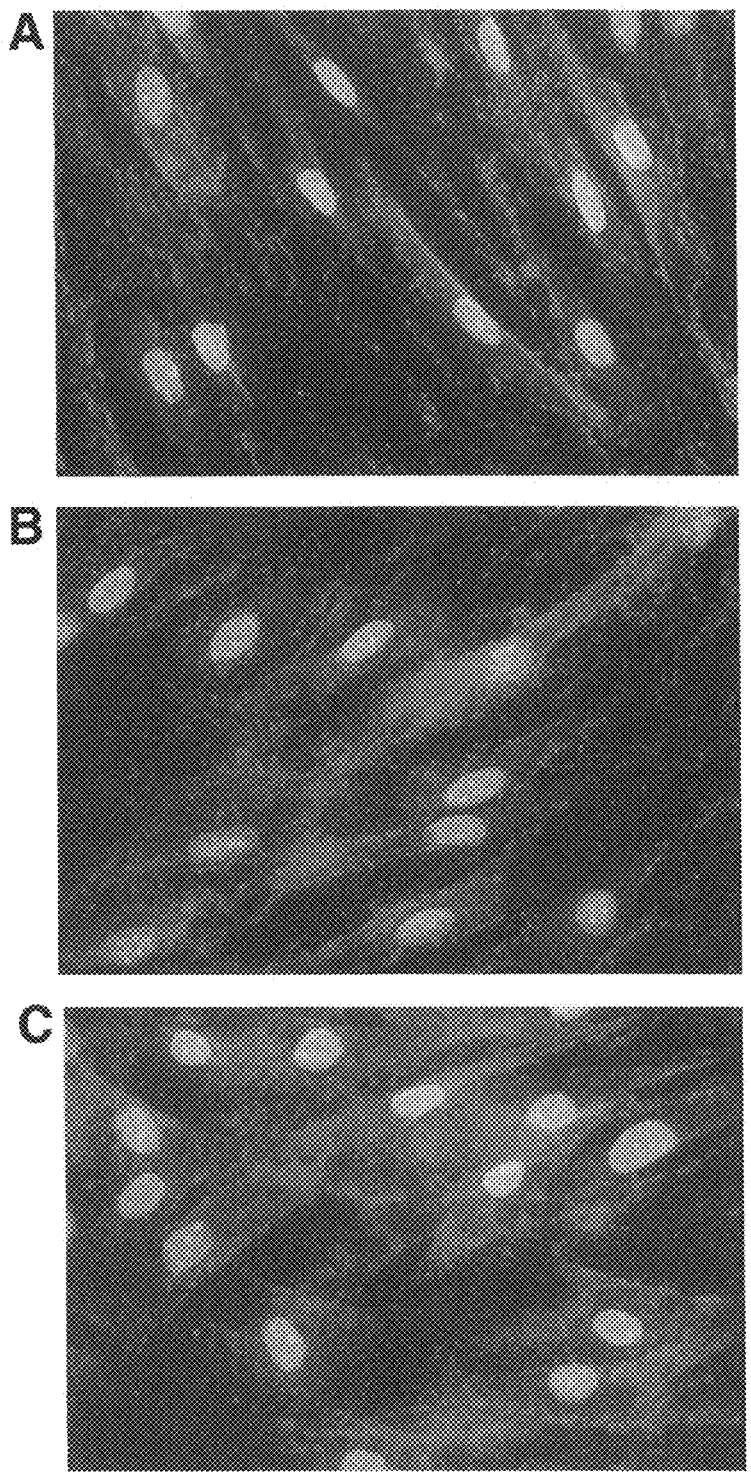
FIG. 1 shows a representative micrograph (×400) depicting immuno-localization of mineralocorticoid receptor (MR) in fibroblasts derived from normal human skin (A), stretch-marked skin (B) and dermal scar tissue (C).

μM spironolactone (F), 50 nM Aldo and 2 μM spironolactone (G), and 1 μM Aldo and 2 μM spironolactone (H).

FIG. 3 (A) shows an agarose gel of cellular mRNA stained for collagen type I mRNA and GAPDH mRNA collected from untreated normal skin fibroblasts (A1), cells treated with 50 nM Aldo (A2), 1 μM Aldo (A3), 2 μM spironolactone (A4), 50 nM Aldo and 2 μM spironolactone (A5), 1 μM Aldo and 2 μM spironolactone (A6), and a bar graph corresponding to these data. (B) shows an agarose gel of cellular mRNA stained for elastin mRNA and GAPDH mRNA collected from untreated normal skin fibroblasts (B1), cells treated with 50 nM Aldo (B2), 1 μM Aldo (B3), 2 μM spironolactone (B4), 50 nM Aldo and 2 μM spironolactone (B5), 1 μM Aldo and 2 μM spironolactone (B6), and a bar graph corresponding to these data. (C) shows a bar graph depicting the deposition of mature, insoluble elastin based on the incorporation of [$^3$H]-valine into insoluble elastin for an untreated control (C1), 2 μM spironolactone (C2), 10 nM Aldo (C3), 10 nM Aldo and 2 μM spironolactone (C4), 50 nM Aldo (C5), 50 nM Aldo and 2 μM spironolactone (C6), 1 μM Aldo (C7), and 1 μM Aldo and 2 μM spironolactone (C8).

FIG. 4 shows representative micrographs (×400) of 7-day-old cultures of fibroblasts derived from patient with stretch marks immuno-stained for elastin using green fluorescein-labeled anti-elastin antibody and nuclei stained using red propidium iodide that are untreated (A), treated with 50 nM Aldo (B), 2 μM spironolactone (C), and 50 nM Aldo and 2 μM spironolactone (D). (E) shows a bar graph depicting the deposition of mature, insoluble elastin as determined by incorporation of [$^3$H]-valine by these cells for untreated control (E1), cells treated with 2 μM spironolactone (E2), 50 nM Aldo (E3), and 50 nM Aldo and 2 μM spironolactone (E4).

FIG. 5 shows representative micrographs (×400) of 7-day-old cultures of fibroblasts derived from dermal scar tissue immuno-stained for elastin using green fluorescein-labeled anti-elastin antibody and nuclei stained using red propidium iodide that are untreated (A), treated with 50 nM Aldo (B), 2 μM spironolactone (C), and 50 nM Aldo and 2 μM spironolactone (D). (E) shows a bar graph depicting the deposition of mature, insoluble elastin as determined by incorporation of [$^3$H]-valine in these cells for untreated control (E1), cells treated with 2 μM spironolactone (E2), 50 nM Aldo (E3), and 50 nM Aldo and 2 μM spironolactone (E4).

FIG. 6 shows representative micrographs (×200) of Movat's pentachrome-stained transverse sections of skin biopsy explants derived from normal abdominal skin of a 30-year-old woman untreated (A), treated with 50 nM Aldo (B), and 50 nM Aldo and 2 μM spironolactone (C); and from 34-year-old woman with abdominal stretch marks untreated (D), treated with 50 nM Aldo (E) and 50 nM Aldo and 2 μM spironolactone (F). Movat's pentachrome stains elastin black, collagen yellow, cells red, and nuclei dark blue.

FIG. 7 shows representative micrographs (×200) of Movat's pentachrome-stained transverse sections of skin biopsy explants derived from the superficial portions of the abdominal dermal scar of a 29-year-old woman untreated (A), treated with 50 nM Aldo (B), and 50 nM Aldo and 2 μM spironolactone (C), and dipper portion of the scar untreated (D), treated with 50 nM Aldo (E), and 50 nM Aldo and 2 μM spironolactone (F). Movat's pentachrome stain shows elastin as black, collagen as yellow, cells red, and nuclei as dark blue.

FIG. 8 shows representative micrographs (×400) of 7-day-old cultures of normal skin fibroblasts immuno-stained for elastin using green fluorescein-labeled anti-elastin antibody and nuclei stained using red propidium iodide that are untreated (A), treated with 1 μg/ml aIGF-IR and 50 ng/ml IGF-I (B), 50 nM Aldo (C), 50 nM Aldo and 5 μM AG1024 (D), 50 ng/ml IGF-I (E), 5 μM AG1024 and 50 ng/ml IGF-I (F), 1 μg/ml aIGF-IR and 50 nM Aldo (G), and 50 nM Aldo and 50 ng/ml IGF-I (H).

Figure 9:
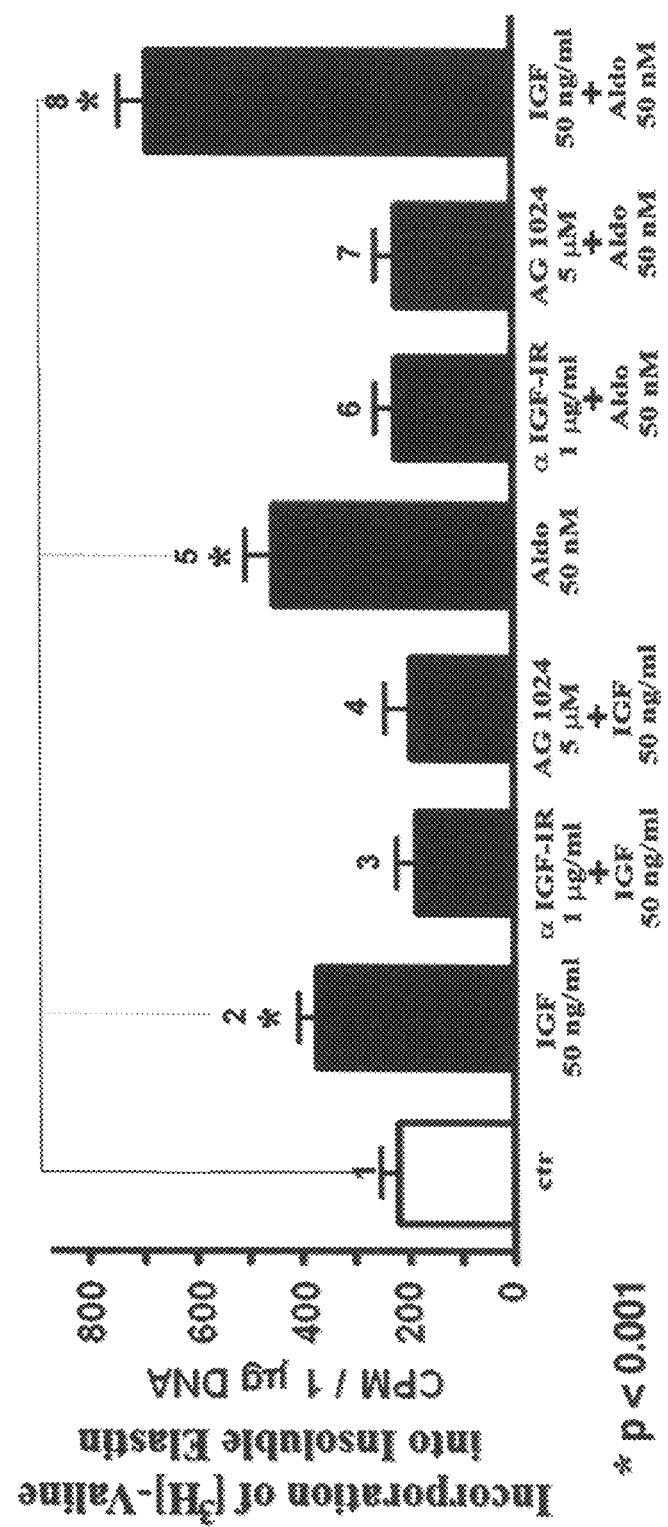

FIG. 9 shows quantitative data representing mature, insoluble elastin from cultured normal skin fibroblasts metabolically labeled with [$^3$H]-valine that are untreated (1), treated with 50 ng/ml IGF-I (2), 50 ng/ml IGF-1 and 1 μg/ml aIGF-IR (3), 50 ng/ml IGF-1 and 5 μM AG1024 (4), 50 nM Aldo (5), 50 nM Aldo and 1 μg/ml aIGF-IR (6), 50 nM Aldo and 5 μM AG1024 (7), and 50 nM Aldo and 50 ng/ml IGF-I (8).

FIG. 10 shows representative micrographs (×400) of 7-day-old cultures of fibroblasts derived from dermal scar immuno-stained for elastin using green fluorescein-labeled anti-elastin antibody and nuclei stained using red propidium iodide that are untreated (A), treated with 10 ng/ml IGF-I (B), 100 ng/ml IGF-I (C), and 10 ng/ml IGF-1 and 50 nM Aldo (D). (E) shows a bar graph depicting the deposition of mature, insoluble elastin as determined by incorporation of [$^3$H]-valine for untreated control (E1), cells treated with 10 ng/ml IGF-I (E2), 100 ng/ml IGF-I (E3), and 10 ng/ml IGF-1 and 50 nM Aldo (E4).

FIG. 11 shows representative micrographs (×200) of Movat's pentachrome-stained transverse sections of skin biopsy explants derived from superficial portions of an abdominal dermal scar of a 29-year-old woman that is untreated (A), treated with 50 nM Aldo (B), 50 nM Aldo and 2 μM spironolactone (C), 5 μM AG1024 (D), 50 nM Aldo and 5 μM AG1024 (E), and 50 nM Aldo, 2 μM spironolactone and 5 μM AG1024 (F).

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must be noted that as used herein, and in the appended claims, the singular forms "a," "an," and "the" include plural reference unless the context clearly dictates otherwise. Thus, for example, reference to a "fibroblast" is a reference to one or more fibroblasts and equivalents thereof known to those skilled in the art.

As used herein, all claimed numeric terms are to be read as being preceded by the term, "about," which means plus or minus 10% of the numerical value of the number with which it is being used. Therefore, a claim to "50%" means "about 50%" and encompasses the range of 45%-55%.

"Administering" when used in conjunction with a therapeutic means to administer a therapeutic directly into or onto a target tissue, or to administer a therapeutic to a patient whereby the therapeutic positively impacts the tissue to which it is targeted. Thus, as used herein, the term "administering," when used in conjunction with aldosterone or any other composition described herein, can include, but is not limited to, providing aldosterone locally by administering aldosterone into or onto the target tissue, providing aldosterone systemically to a patient by, for example, intravenous injection whereby the therapeutic reaches the target tissue or providing aldosterone in the form of the encoding sequence thereof to the target tissue (e.g., by so-called gene-therapy techniques). "Administering" a composition may be accomplished by any mode including parenteral administration including injection, oral administration, topical administration, or by any other method known in the art including for example electrical deposition (e.g., ionotophoresis) and ultrasound (e.g., sonophoresis). In certain embodiments, the compositions described herein may be administered in combination with another form of therapy, including for example radiation therapy, infrared therapy, ultrasound therapy, or any other therapy know in the art or described herein.

In certain embodiments, the compositions may be combined with a carrier. A "carrier" as used herein may include, but is not limited to, an irrigation solution, antiseptic solution, other solution time released composition, elution composition, bandage, dressing, colloid suspension (e.g., a cream, gel, or salve) internal or external dissolvable sutures, dissolvable beads, dissolvable sponges and/or other materials or compositions known now or hereafter to a person of ordinary skill in the art.

The term "animal" as used herein includes, but is not limited to, humans and non-human vertebrates, such as wild, domestic, and farm animals.

The term "improves" is used to convey that the present invention changes either the appearance, form, characteristics and/or the physical attributes of the tissue to which it is being provided, applied or administered. The change in form may be demonstrated by any of the following, alone or in combination: enhanced appearance of the skin, increased softness of the skin, increased turgor of the skin, increased texture of the skin, increased elasticity of the skin, decreased wrinkle formation and increased endogenous elastin production in the skin, increased firmness and resiliency of the skin.

The term "inhibiting" includes the administration of a compound of the present invention to prevent the onset of the symptoms, alleviating the symptoms, or eliminating the disease, condition or disorder.

By "pharmaceutically acceptable," it is meant that the carrier, diluent or excipient must be compatible with the other ingredients of the formulation and not deleterious to the recipient thereof. By "excipient," it is meant any inert or otherwise non-active ingredient, which can be added to the active ingredient which may improve the overall composition's properties, such as improving shelf-life, improving retention time at the application site, improving flowability, improving consumer acceptance, et alia.

Unless otherwise indicated, the term "skin" means that outer integument or covering of the body, consisting of the dermis and epidermis and resting upon subcutaneous tissue.

As used herein, the term "therapeutic" means an agent utilized to treat, combat, ameliorate, prevent or improve an unwanted condition or disease of a patient.

A "therapeutically effective amount" or "effective amount" of a composition is a predetermined amount calculated to achieve the desired effect, i.e., to increase production of elastin or the deposition of elastic fibers. For example, a therapeutic effect may be demonstrated by increased elastogensis, increased cellular proliferation, increased digestion or resorption of scar material, reduction of symptoms and sequellae as well as any other therapeutic effect known in the art. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, the physical characteristics of the patient (height, weight, etc.), and the condition being treated. It will be understood that the effective amount administered will be determined by the physician in light of the relevant circumstances, including the condition to be treated, the choice of compound to be administered, and the chosen route of administration, and therefore, the dosage ranges provided are not intended to limit the scope of the invention in any way. A "therapeutically effective amount" of compound of this invention is typically an amount such that when it is administered in a physiologically tolerable excipient composition, it is sufficient to achieve an effective systemic concentration or local concentration in the tissue.

In certain embodiments, the dose of aldosterone is in the range of 1-2 µM. In other embodiments, the dose of spironolactone is in the range of 10-20 µM. However, these dosages may be adjusted since there is virtually no danger of a systemic overdose. As such, aldosterone may be administered, either alone or in combination with any other active agent, at 0.01 µM, 0.1 µM, 1.0 µM, 2.0 µM, 5.0 µM, 10.0 µM, 20.0 µM, 50 µM, 100 µM, and any range therebetween. Similarly, spironolactone may be administered at any suitable dose, either alone or in combination with another active agent such as aldosterone at 0.01 µM, 0.1 µM, 1.0 µM, 2.0 µM, 5.0 µM, 10 µM, 20 µM, 50 µM, 100 µM, 200 µM and any range therebetween. Those of ordinary skill in the art recognize that such dosages can be calculated per liter of compound.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function. As used herein, "tissue," unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity. See for example, U.S. Provisional Application 61/059,288 and 61/059,475 filed concurrently herewith on Jun. 6, 2008, and incorporated by reference in their entirety.

Embodiments presented herein are generally directed to compositions including at least one mineralocorticoid and methods of using such compositions for the treatment of tissue.

The composition of various embodiments may include any mineralocorticoid known in the art, including, for example, aldosterone. Other embodiments include pharmaceutical compositions, including a mineralocorticoid and a pharmaceutically acceptable carrier, diluent, or excipient, and in certain embodiments, the compositions or pharmaceutical compositions may include secondary active agents which enhance or improve the function of the mineralocorticoid. Such compositions may be formulated in any way. For example, in various embodiments, the compositions may be formulated as a liquid, solid, gel, lotion or cream, and the formulation of the composition may vary among embodiments depending on the mode of administration of the compositions.

In some embodiments, corticosteroids having at least some mineralocorticoid activity, such as, for example, deoxycorticosterone and fludrocortisones may be used in place of or in combination with the mineralocorticoids of the compositions and pharmaceutical compositions described above. Without wishing to be bound by theory, such corticosteroids may affect tissue treated therewith in the same manner as mineralocorticoids, such as aldosterone.

In various embodiments, the mineralocorticoid may interact with cells, such as, for example, fibroblasts and the like, and induce the production of elastin by these cells or increase the deposition of the elastin into the extracellular space surrounding these cells. In certain embodiments, aldosterone may interact with such cells in a mineralocorticoid receptor (MR) independent manner. Thus, in some embodiments, aldosterone may be administered in combination with a secondary active agent. As used herein the term secondary active agent is intended to mean a pharmacologically active compound administered in conjunction with a mineralocorticoid. As such, in certain embodiments, secondary active agents include those that inhibit collagen synthesis by inhibiting MR stimulation or deposition associated with MR stimulation, reduce the synthesis or deposition of collagen in activated cells, inhibiting factors associated with collagen synthesis or factors associated with collagen deposition and combinations of these, while maintaining or enhancing production of elastin or elastin fibers. Without wishing to be bound by theory, inhibition of collagen synthesis or deposition of collagen may enhance the effectiveness of various embodiments by producing a net increase in deposition of elastin fibers while reducing the net deposition of collagen which may be associated with, for example, scar tissue. Therefore, in some embodiments, aldosterone may be administered in combination with an agent that inhibits MR activation or collagen synthesis associated with MR stimulation or inhibits collagen synthesis throughout effected cells. For example, in an embodiment, aldosterone may be administered in combination with mineral corticorticoid receptor antagonist such as eplerenone, canrenone, spirolactone et alia, which are synthetic lactone drugs that act as a competitive aldosterone antagonist. In yet another embodiment, a mineralocorticoid such as aldosterone may be administered in combination with an MR binding antibody, such as, for example, mineralocorticoid receptor antibody (H10E4C9F) mineralocorticoid receptor antibody (H3122), Mouse Anti-Human NR3C2 Monoclonal Antibody (Clone 2B5), Mouse Anti-Human Mineralocorticoid R (aa 1-670 Clone 385707), et alia disclosed herein or described in the art.

The mineralocorticoid, or aldosterone, of various embodiments may interact with cells, such as, for example, fibroblasts in an insulin growth factor receptor I (IGF-IR) dependent manner. Therefore, in some embodiments, aldosterone may be administered in combination with an agent that enhances the pro-elastogenic effect of IGF-IR stimulation or stimulates the synthesis of IGF-IR, IGF-IR kinase, or other components of the IGF-IR signaling pathway and combinations thereof. Without wishing to be bound by theory, enhancing the ability of a cell to be stimulated by aldosterone by increasing the expression of IGF-IR or the sensitivity of IGF-IR on the cell surface may increase the net deposition of elastin fibers in treated tissue thereby enhancing the effectiveness of such treatment. By "increased expression," it is intended to mean an effect on any pathway that leads to an increase of the number of functional protein molecules, and includes for example, increased IGF-IR mRNA synthesis, increased IGF-IR mRNA stability, increased anabolism of the protein, decreased catabolism of the protein, and any other pathway by which expression can be increased. By "increased sensitivity," it is intended to mean increasing the responsiveness of the protein to its ligand, which can occur in any manner including crosslinking of receptors, conformational changes in the receptors, phosphorylation/dephosphorylation of the receptor, or any other mechanism by which sensitivity can be increased.

The compositions described in the embodiments above may be administered to any tissue in need of enhanced elastin deposition. For example, in some embodiments, such compositions may be administered to skin, skin cells or tissues associated with skin to treat, for example, scar tissue, wrinkles, or excessively stretched skin. In other embodiments, the composition may be administered to cells and tissues associated with the gastrointestinal tract or genitourinary system, such as, for example, strictures caused by trauma or excessive collagen formation, and prostate enlargement.

In one embodiment, the compositions disclosed herein are used to treat keloids. Specifically, the keloid growth can be treated with corticosteroids to decrease collagen production. Subsequently, collagenase can be administered at a site of scarring and then the aldosterone and spironolactone can be administered. In some embodiments, aldosterone is administered locally as a cream/injection and spironolactone is administered as a tablet.

In embodiments wherein aldosterone is administered in combination with a secondary active agent, the combination may be administered as a single unit wherein the aldosterone and secondary active agent are combined to form a single, tablet or injectable emulsion, for example. In other embodiments, aldosterone may be administered separately from the secondary active agent, and in particular embodiments, the one component may be administered at a separate time from the other component. For example, in one embodiment, the secondary active agent may be administered first to prepare the target tissue by, for example, increasing IGF-IR expression, and aldosterone may be administered at a later time.

Methods of embodiments generally include administering a composition or pharmaceutical composition including a mineralocorticoid to a subject or patient in need of treatment. Pharmaceutical compositions useful in various embodiments may be administered to treat, ameliorate, or alleviate symptoms associated with various diseases that may be identified by inability to produce elastin or elastin fibers, or functional elastin or elastin fibers, loss of functional elastin or elastin fibers, or the lack or loss of deposition of elastin or elastin fibers in the subject's tissue. Such diseases include diseases of the skin, such as, but not limited to, aging, stretch marks, overly stretched skin, sun damaged skin, scar tissue, supravalvular aortic stenosis (SVAS), Williams-Beuren syndrome (WBS), Cutis Laxa, Marfan disease, GM-1-gangliosidosis, Morquio B, Hurler disease, Costello syndrome, Ehlers Danlos syndrome, and pseudoxanthoma elasticum (PXE). The pharmaceutical composition may be administered by any method known in the art including, for example, systemic administration, local administration, and topical administration.

Various embodiments, therefore, include pharmaceutical compositions having a mineralocorticoid or combination of a mineralocorticoid and a secondary active agent of embodiments described above, and a pharmaceutically acceptable carrier, diluent or excipient, or an effective amount of a pharmaceutical composition including a mineralocorticoid or combination of a mineralocorticoid and a secondary active agent, as defined above, and a pharmaceutically acceptable carrier, diluent or excipient.

The compounds of the various embodiments may be administered in a conventional manner by any route by which they retain activity. For example, a mineralocorticoid or combination of a mineralocorticoid and a secondary active agent of embodiments may be administered by routes including, but not limited to, topical, parenteral, subcutaneous, intravenous, intraperitoneal, transdermal, oral, buccal, inhalation, depot injection, or implantation. Thus, modes of administration for the compounds (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal and topical forms such as patches and creams.

Specific modes of administration will depend on the indication and other factors including the particular compound being administered. The selection of the specific route of administration and the dose regimen is to be adjusted or titrated by the clinician according to methods known to the clinician in order to obtain the optimal clinical response. For example, in embodiments wherein the compositions are used to treat skin wrinkled by aging, or stretch marked, scarred, overly stretched, or sun damaged skin, the compositions may be administered topically using, for example, a lotion. In other embodiments wherein the compositions are used to treat a disease having more systemic effects such as, supravalvular aortic stenosis (SVAS), Williams-Beuren syndrome (WBS), Cutis Laxa, Marfan disease, GM-1-gangliosidosis, Morquio B, Hurler disease, Costello syndrome, Ehlers Danlos syndrome, pseudoxanthoma elasticum (PXE) or diseases of the gastrointestinal tract or genitourinary system the compositions may be administered systemically, using for example, a tablet or injectable emulsion. In still other embodiments, the compositions may be administered both systemically and topically.

The amount of the compositions of various embodiments to be administered is an amount that is therapeutically effective, and the dosage administered may depend on the characteristics of the subject being treated. For example, the dosage may depend on the particular animal treated, the age, weight, and health of the subject, the types of concurrent treatment, if any, and frequency of treatments. Many of these factors can be easily determined by one of skill in the art (e.g., by the clinician).

Various pharmaceutical formulations include those containing an effective amount of the compounds and a suitable carrier, diluent, or excipient can be in solid dosage forms including, but not limited to, tablets, capsules, cachets, pellets, pills, powders and granules; topical dosage forms including, but not limited to, solutions, powders, fluid emulsions, fluid suspensions, semi-solids, ointments, pastes, creams, lotions, gels, jellies, and foams; and parenteral dosage forms including, but not limited to, solutions, suspensions, emulsions, and dry powders. The active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like.

The means and methods for administration of such pharmaceutical formulations are known in the art and an artisan can refer to various pharmacologic references, such as, for example, *Modern Pharmaceutics*, Banker & Rhodes, Marcel Dekker, Inc. (1979) and *Goodman & Gilman's The Pharmaceutical Basis of Therapeutics*, 6th Edition, MacMillan Publishing Co., New York (1980) for guidance. For example, in some embodiments, the compounds can be formulated for parenteral administration by injection, and in one embodiment, the compounds can be administered by continuous infusion subcutaneously over a period of about 15 minutes to about 24 hours. In another embodiment, formulations for injection can be presented in unit dosage form, e.g., in ampoules or in multi-dose containers, with an added preservative. In still other embodiments, the compositions can take such forms as suspensions, solutions or emulsions in oily or aqueous vehicles, and can contain formulatory agents such as suspending, stabilizing and/or dispersing agents.

For certain embodiments encompassing oral administration, the compounds can be formulated readily by combining these compounds with pharmaceutically acceptable carriers known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers. If desired, disintegrating agents, such as, but not limited to, the cross-linked polyvinyl pyrrolidone, agar, or alginic acid or a salt thereof, such as sodium alginate, may be added.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally also include, but are not limited to, push-fit capsules made of gelatin, as well as soft, sealed capsules made of gelatin and a plasticizer, such as glycerol or sorbitol. The push-fit capsules can contain the active ingredients in a mixture with filler such as binders and/or lubricants, such as, for example, talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, for example, tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions, such as, suppositories or retention enemas, for example, containing conventional suppository bases such as cocoa butter or other glycerides.

In addition to the formulations described previously, the compounds of the present invention can also be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In transdermal administration, the compounds of the present invention can, for example, be applied to a plaster, or can be applied by transdermal, therapeutic systems that are consequently supplied to the organism.

Pharmaceutical compositions of the compounds also can include suitable solid or gel phase carriers or excipients. Examples of such carriers or excipients include but are not limited to calcium carbonate, calcium phosphate, gelatin, and polymers such as, for example, polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

This invention and embodiments illustrating the method and materials used may be further understood by reference to the following non-limiting examples.

EXAMPLES

In vitro studies described herein, employed cultures of human skin fibroblasts and organ cultures of skin explants derived from normal individuals and patients with stretch marks and dermal scars.

Materials:

All chemical-grade reagents were obtained from Sigma (St. Louis, Mo.). αMEM medium, fetal bovine serum (FBS), 0.2% trypsine—0.02% EDTA and other cell culture products were obtained from GIBCO Life Technologies (Burlington, Canada). Polyclonal antibody to tropoelastin was purchased from Elastin Products Company, Inc. (Owensville, Mo.). Secondary antibody fluorescein-conjugated goat anti-rabbit (GAR-FITC) was purchased from Sigma (St. Louis, Mo.). DNeasy Tissue system for DNA assay and RNeasy Mini Kit for isolation of total RNA were purchased from Qiagen (Mississauga, Canada). Expression probe for elastin was purchased from Applied Biosystems (Foster City, Calif.). The radiolabeled reagents, [$^3$H]-valine, and [$^3$H]-thymidine were purchased from Amersham Canada Ltd. (Oakville, Canada).

Methods:

Institutional Review Board (IRB) approval and patient informed consent were obtained for this study that required small fragments of skin excess collected during plastic surgery procedures. Guidelines for the protection of human subjects of the Department of Health and Human Services (DHHS) and of the Declaration of Helsinki were strictly followed in obtaining tissues for this investigation.

Cell Cultures:

Biological effects of aldosterone and spironolactone were tested in cultures of dermal fibroblasts derived from normal skin, stretch-marked skin and dermal scars derived from Caucasian females, of different ages ranging from 30-38 years old. All fibroblasts were originally isolated by allowing them to migrate out of skin explants and then passaged by trypsinization and maintained in alpha-minimum essential medium supplemented with 20 mM Hepes, 1% antibiotics and antimycotics, 1% L-Glutamate and 2% fetal bovine serum (FBS) as previously described Hinek et al. "Impaired elastic-fiber assembly by fibroblasts from patients with either Morquio B disease or infantile GM1-gangliosidosis is linked to deficiency in the 67-kD spliced variant of beta-galactosidase." Am J Hum Genet. 2000 July; 67(1):23-36 hereby incorporated by reference in its entirety. In all experiments, consecutive passages 3-4 were tested. Cells were densely plated ($50 \times 10^5$ cells/dish) to reach confluency and then cultured for 7 days in the presence and absence of different concentrations of (10 nM-1 μM) aldosterone, 2 μM spironolactone, alone or in combinations with other reagents, as described in figure legends.

Organ Cultures of Explants Derived from Surgical Biopsies of Human Skin:

In order to further test whether aldosterone and spironolactone would penetrate into skin tissue and affect elastogenesis, fragments of normal skin, stretch-marked skin and dermal scars were tested in organ culture system. Skin fragments were cut into multiple 1 mm$^2$ pieces and placed on top of metal grids immersed in culture medium containing 5% FBS and maintained for 10 days in the presence and absence of and then cultured for 7 days in the presence of 50 nM aldosterone, and 2 μM spironolactone, alone or in combinations, as described in figure legends. The media were changed every second day.

All organ cultures were fixed in 1% buffered formalin and their transversal serial histological sections were stained with Movat's pentachrome as previously described in Hinek et al. "Proteolytic digest derived from bovine Ligamentum Nuchae stimulates deposition of new elastin-enriched matrix in cultures and transplants of human dermal fibroblasts" J Dermatol Sci. September 2005; 39(3):155-66 hereby incorporated by reference in it's entirety. Morphometric analysis was performed as described above. In each analyzed group (three explants from each patient) low-power fields (1 mm$^2$) of 20 serial sections stained with Movat's pentachrome were analyzed and all structures stained black (elastic fibers) were counted.

Assessment of Collagen I and Elastin mRNA Levels:

Fibroblasts were cultured to confluency in medium with 2% FBS and then in serum-free medium for 24 hours. The medium was changed again and cells were incubated for the next 24 hours in the presence and absence of in the presence of 50 nM and 1 μM aldosterone, and 2 μM spironolactone, alone or in combinations, as described in figure legend. At the end of the incubation period total RNA was extracted using the RNeasy Mini Kit, according to manufacturer's instructions. Steady-state levels of elastin mRNA were then analyzed by One-Step RT-PCR analysis. Briefly, 1 µg of total RNA was added to each one step RT-PCR (Qiagen One-Step RT-PCR Kit), and reactions were set up according to manufacturer's instructions in a total volume of 25 µl. The reverse transcription step was performed for elastin, and GAPDH reactions at 50° C. for 30 minutes, followed by 15 minutes at 95° C. The elastin PCR reaction (sense primer: 5' GGTGCG-GTGGTTCCTCAGCCTGG-3' (SEQ ID NO: 1), antisense primer: 5'-GGGCCTTGAGATAC-CCCAGTG-3' (SEQ ID NO: 2); designed to produce a 255 bp product) was performed under the following conditions: 25 cycles at 94° C. denaturation for 20 s, 63° C. annealing for 20 s, 72° C. extension for 1 min; 1 cycle at 72° C. final extension for 10 min.

The collagen Type I PCR reaction (sense 5'-CCCAC-CAATCACCTGCGTACAGA-3' (SEQ ID NO: 3), antisense primer: 5'-TTCTTGGTCGGTGGGTGACTCTGA-3' (SEQ ID NO: 4)) was performed under the following conditions: 20 cycles at 94° C., denaturation for 30 s, 58° C. annealing for 30 s, 72° C. extension for 10 min; 1 cycle at 72° C. final extension for 10 min. The GAPDH PCR reaction (sense primer: 5'-TC-CACCACCCTGTTGCTGTAG-3' (SEQ ID NO: 5), antisense primer: 5'-GACCACAGTCCATGCCATC-ACT-3' (SEQ ID NO: 6); designed to produce a 450 bp product) was performed under the following conditions: 21 cycles at 94° C. denaturation for 20 s, 58° C. annealing for 30 s, 72° C. extension for 1 min; 1 cycle at 72° C. final extension for 10 min. 5 µl. Samples of the elastin and GAPDH PCR products from each reaction, were run on a 2% agarose gel and post-stained with ethidium bromide. The amount of elastin mRNA was standardized relative to the amount of GAPDH mRNA.

Assessment of Elastic Fiber Content by Immunohistochemistry:

7-day-old cultures of fibroblasts, which produce abundant ECM, were assessed. All cultures were fixed in cold 100% methanol at −20° C. for 30 min, and then incubated for 1 hour with 2 µg/ml of polyclonal antibody to tropoelastin. Cultures were then incubated for an additional hour with appropriate fluorescein-conjugated secondary antibody (GAR-FITC). Nuclei were counterstained with propidium iodide. Morphometric analysis of five separate cultures in each experimental group, immunostained with antibodies recognizing extracellular matrix components, was performed using a computerized video analysis system (Image-Pro Plus software 3.0, Media Cybernetics, Silver Spring, Md.) as described previously in Hinek et al. "Decreased elastin deposition and high proliferation of fibroblasts from Costello syndrome are related to functional deficiency in the 67-kD elastin-binding protein." Am J Hum Genet. 2000 March; 66(3):859-72 and Hinek and Wilson, "Impaired elastogenesis in Hurler disease: dermatan sulfate accumulation linked to deficiency in elastin-binding protein and elastic fiber assembly." Am J. Pathol. 2000 March; 156(3):925-38 both of which are hereby incorporated by reference in their entireties.

Radioactive Metabolic Labeling and Quantification of the Newly Deposited Insoluble Elastin:

Quintuplicate, 4 day-old cultures of dermal fibroblasts maintained in the presence and absence of indicated reagents were additionally exposed for the 3 following days to 20 µCi [$^3$H]-valine. At the end of incubation period, the cell layers were extensively washed with PBS, scraped and boiled in 500 µl of 0.1 N NaOH for 30 minutes, to solubilize all matrix components except elastin. The resulting pellets containing the insoluble elastin were then solubilized by boiling in 200 µl of 5.7 N HCl for 1 hour, and the aliquots were mixed in scintillation fluid and counted. Aliquots taken from each culture were also used for DNA determination, according to Rodems et al., using the DNeasy Tissue System from Qiagen. Final results reflecting amounts of metabolically labeled insoluble elastin in individual cultures were normalized per their DNA content, and expressed as CPM/1 µg DNA.

Statistical Analysis:

In all above mentioned quantitative assays, means and standard deviations (expressed as Mean±SD) were calculated and statistical analyses were carried out by ANOVA to establish whether detected differences were statistically significant.

Example 1

Expression of MR in cultured human dermal fibroblasts was established by immuno-staining of MR of dermal fibroblasts. FIG. 1 shows a representative micrograph at ×400 magnification, depicting immuno-localization of MR in fibroblasts derived from normal human skin (A), stretch-marked skin (B) and dermal scar tissue (C). In FIG. 1, anti-MR green-fluorescein labeled antibodies show the localization and concentration of MR in fibroblasts whose nuclei have been stained with red propidium iodide. These data show that MR is expressed in approximately equal concentrations in each tissue type.

To show that treatment of normal skin fibroblasts with aldosterone increases in levels of elastin and consequently increase deposition of elastic fibers, cultured dermis fibroblast cells were treated with increasing concentrations of aldosterone (Aldo) and incubated for 7 days. Anti-elastin green-fluorescein labeled antibodies were then used to detect elastin fibers, and red propidium iodide was used to stain the nuclei of the cells. FIG. 2, Panels A-D, show that the concentration of elastin is increased in an aldosterone concentration specific manner. Thus, as the aldosterone concentration increases so does the concentration of elastin in treated cells. FIG. 2, Panels E-H show that addition of a MR inhibitor, spironolactone (Spiro), did not alter elastin deposition in cells treated with increasing concentrations of aldosterone, indicating that aldosterone may enhance elastin deposition in a MR-dependent manner. These results also suggest that aldosterone mediated elastin deposition may be effected without the corresponding increase in collagen deposition associated with MR stimulation.

To confirm these results, the steady-state level of collagen type I and elastin mRNA in cells treated with either aldosterone or a combination of aldosterone and spironolactone were determined. FIG. 3, Panel A shows a representative agarose gel stained to show collagen type I mRNA in the total mRNA collected various treated cells. GAPDH mRNA is also stained as a control. The collagen type I mRNA concentration is provided on the bar graph below. These data clearly show net increase of collagen type I mRNA in treated cells corresponding to the increasing concentrations of aldosterone only. In contrast, the concentration of collagen type I mRNA in cells treated with aldosterone in combination with spironolactone is maintained at approximately control levels. FIG. 3, Panel B shows that the concentration of elastin mRNA increases in an aldosterone concentration dependent manner both when aldosterone is administered alone and when aldosterone is administered in combination with spironolactone. FIG. 3, Panel C shows the deposition of mature, insoluble elastin in cells treated with either aldosterone alone or aldosterone in combination with spironolactone by detecting the net incorporation of [$^3$H]-valine into mature elastin. These results indicate that the deposition of mature elastin may be enhanced by the administration of aldosterone in combination with spironolactone (Lanes 4, 6 and 8) in comparison with aldosterone alone (Lanes 3, 5 and 7).

The effect of treatment with aldosterone and aldosterone in combination with spironolactone on stretched marked skin was tested using cultured cells derived from fibroblast from a patient with stretch marks. As can be seen in FIG. 4, Panels A-D, administration of 50 nM aldosterone alone (Panel B) or in combination with 2 μM spironolactone (Panel D) show an increase in elastin stained by anti-elastin green-fluorescein labeled antibodies over an untreated control (Panel A) or cells treated with 2 μM spironolactone only (Panel C). Panel E shows a bar graph representing the effects of the deposition of mature, insoluble elastin as the result of administration of 50 nm aldosterone alone or in combination with 2 μM spironolactone as indicated by incorporation of [$^3$H]-valine into mature elastin. These results show that the concentration of mature elastin is increased by the administration of aldosterone (Lane 3), and that this effect is enhanced by the administration of aldosterone in combination with spironolactone (Lane 4).

Similar results were obtained from cultured cells derived from dermal scar tissue. FIG. 5, Panels A-D show that administration of 50 nM aldosterone alone (Panel B) or in combination with 2 μM spironolactone (Panel D) show an increase in elastin stained by anti-elastin green-fluorescein labeled antibodies over an untreated control (Panel A) or cells treated with 2 μM spironolactone only (Panel C). Panel E again shows that the deposition of insoluble mature elastin is enhanced when aldosterone is administered alone (Lane 3) or in combination with spironolactone (Lane 4) when incorporation of [$^3$H]-valine into mature elastin is monitored.

Representative micrographs of Movat's pentachrome-stained transverse sections of skin biopsy explants derived from normal abdominal skin of a 30-year-old woman and from a 34-year-old woman with abdominal stretch marks maintained for 10 days are shown in FIG. 6, Panels A-F. Movat's pentachrome stains elastin black, collagen yellow, cells red and nuclei dark blue. These data show that skin explants maintained in the presence of 50 nM aldosterone from normal skin (Panel B) and stretch marked skin (Panel E) contain thicker and longer elastic fibers than those present in respective untreated explants (normal skin (Panel A) and stretched marked skin (Panel D)). Addition of 2 μM spironolactone to skin explants treated with 50 nM aldosterone enhances the deposition of elastin in both normal (Panel C) and stretched marked skin (Panel F).

Similar results were obtained for explants derived from abdominal dermal scar of a 29-year-old woman. FIG. 7 shows representative micrographs of Movat's pentachrome-stained transverse sections of skin biopsy, the superficial portion of the scar (Panels A-C) and dipper portion of the scar (Panels D-F) maintained for 10 days. In control medium (Panels A and D) the extracellular matrix of explants consists of collagen bundles and not elastic fibers. Explants maintained in the presence of 50 nM aldosterone (Panels B and E) show numerous elastic fibers, both in sub-epidermal and in a deep layer of the dermal scar. This effect is enhanced in explants that were treated with 50 nM aldosterone in combination with 2 μM spironolactone (Panels C and F) as these samples contain even more elastic fibers than those treated with aldosterone alone.

Example 2

To determine the mechanism by which aldosterone stimulates elastin synthesis and deposition, the effect of blocking IGF-IR was determined.

FIG. 8, Panels A-H show representative micrographs of 7-day-old fibroblast cell cultures of normal skin fibroblasts immuno-stained with anti-elastin green fluorescein-labeled antibody and nuclei stained with the red propidium iodide. These results show that the MR-independent action of aldosterone involves facilitation of intracellular signals induced by the insulin-growth factor receptor I (IGF-IR). Panel E shows that administration of 50 ng/ml IGF-I to cultured fibroblast cells enhances the deposition of elastin in comparison with an untreated control (Panel A). This effect is inhibited by administration of either an IGF-IR blocking antibody (αIGF-IR) (Panel B) or an IGF-IR kinase inhibitor (AG1024) (Panel F). Similarly, the enhanced deposition of elastin observed when cultured fibroblast cells are treated with 50 nM aldosterone (Panel C) in comparison to an untreated control (Panel A) are inhibited by administration of either 1 μg/ml αIGF-IR (Panel G) or 5 μM AG1024 (Panel D). No inhibition is observed in cells treated with 50 ng/ml IGF-1 and 50 nM aldosterone (Panel H).

These results are confirmed when deposition of mature, insoluble elastin is quantified by incorporation of [$^3$H]-valine as shown in FIG. 9. These results show that mature elastin concentrations are maintained at or below control levels (Lane 1) when either αIGF-IR or AG1024 are administered to these cells (Lanes 3, 4, 6 and 7), and that this inhibition of elastin production cannot be overcome by administration of IGF-I (Lanes 3 and 4) or aldosterone (Lanes 6 and 7) even though IGF-I alone (Lane 2) and aldosterone alone (Lane 5) show improved mature elastin concentrations over untreated control (Lane 1). FIG. 9 also shows that elastin deposition can be enhanced over IGF-I alone (Lane 2) or aldosterone alone (Lane 5) by administration of aldosterone in combination with IGF-I (Lane 8). These results strongly suggest that the pro-elastogenic, MR-independent action of aldosterone involves facilitation of intracellular signals induced by IGF-IR.

The effect of IGF-I on deposition of elastin in dermal scar derived fibroblasts was further elucidated by observing the effect of increasing concentrations of IGF-I on these cells as illustrated in FIG. 10. Panels A-D show 7-day-old cultured dermal scar derived fibroblast cells immuno-stained with anti-elastin green fluorescein-labeled antibody and nuclei stained with the red propidium iodide. Panels B and C show an increase in elastin depositions as a result of administration of 10 ng/ml IGF-I (Panel B) and even greater elastin deposition as a result of administration of 100 ng/ml IGF-I (Panel C) over an untreated control (Panel A). Panel D shows that administration of 50 nM aldosterone enhances the effect of administration of 10 ng/ml of IGF-I alone (Panel B) when these agents are administered in combination. Panel E shows a dose dependent increase in deposition of mature, insoluble elastin based on the concentration of IGF-I (Lanes 2 and 3) over untreated control (Lane 1) and that this effect of 10 ng/ml IGF-I is enhanced by the addition of 50 nM aldosterone (Lane 4) when quantified using an [$^3$H]-valine incorporation assay.

FIG. 11 shows representative micrographs of Movat's pentachrome-stained transverse sections of skin biopsy explants derived from abdominal dermal scar of 29-year-old woman. Panels A-C demonstrate that treatment with aldosterone increases in deposition of both collagen (yellow) and elastin (black) (Panel B) when compared to an untreated control (Panel A), and that administration of aldosterone in combination with spironolactone (Panel C) enhances the deposition of elastin (black) without increasing the deposition of collagen (yellow). Panel C may also indicate that inhibition of collagen deposition coincides with a net increase in deposition of elastic fibers. Panels D-F show that this effect is not observed in cells treated AG1024 as no net increase in elastin deposition is observed. These results further confirmed that the pro-elastogenic effect of aldosterone is induced via IGF-IR mediated signaling.

These data suggest that the pro-elastogenic effect of aldosterone is induced via IGF-IR-mediated signaling. Because aldosterone applied in conjunction with spironolactone enhanced a net elastogenesis even in cultures of fibroblasts derived from patients with severe stretch marks and dermal scar tissue, these two factors may be considered in therapies aimed at boosting elastic fibers formation in adult human skin. Since both drugs are small, and lipid-soluble molecules may be used in the topical creams.

Although the present invention has been described in considerable detail with reference to certain preferred embodiments thereof, other versions are possible. Therefore, the spirit and scope of the appended claims should not be limited to the description and the preferred embodiments disclosed herein.

What is claimed is:

1. A method for increasing the net deposition of elastin in skin comprising:
administering an effective amount of a collagen inhibitor and an effective amount of deoxycorticosterone to the skin of a subject affected by a condition selected from the group consisting of keloids, aging, stretch marks, overly stretched skin, sun damaged skin, scar tissue, supravalvular aortic stenosis (SVAS). Williams-Beuren syndrome (WBS), Cutis Laxa, Marfan disease, GM-1-gangliosidosis, Morquio B, Hurler disease, Costello syndrome, Ehlers Danlos syndrome, pseudoxanthoma elasticum (PXE), and combinations thereof, wherein the net deposition of elastin is increased in the skin.

2. The method of claim 1, wherein the deoxycorticosterone affects the skin in a mineralocorticoid receptor independent manner.

3. The method of claim 1, wherein the deoxycorticosterone and the collagen inhibitor are administered simultaneously.

4. The method of claim 1, wherein the collagen inhibitor is administered prior to the deoxycorticosterone.

5. The method of claim 1, wherein the collagen inhibitor is selected from the group consisting of spironolactone, eplerenone, canrenone and a mineralocorticoid neutralizing antibody.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: elastin sense primer

<400> SEQUENCE: 1
ggtgcggtgg ttcctcagcc tgg                                           23

<210> SEQ ID NO 2
<211> LENGTH: 14
<212> TYPE: DNA
<213> ORGANISM: Artificial Sequence
<220> FEATURE:
<223> OTHER INFORMATION: elastin antisense primer

<400> SEQUENCE: 2
gggccttgag atac                                                     14

<210> SEQ ID NO 3
<211> LENGTH: 23
<212> TYPE: DNA
<213> ORGANISM: Artificial Sequence
<220> FEATURE:
<223> OTHER INFORMATION: collagen sense primer

<400> SEQUENCE: 3
cccaccaatc acctgcgtac aga                                           23

<210> SEQ ID NO 4
<211> LENGTH: 24
<212> TYPE: DNA
<213> ORGANISM: Artificial Sequence
<220> FEATURE:
<223> OTHER INFORMATION: collagen antisense primer

<400> SEQUENCE: 4
ttcttggtcg gtgggtgact ctga                                          24

<210> SEQ ID NO 5
<211> LENGTH: 21
<212> TYPE: DNA
<213> ORGANISM: Artificial Sequence
<220> FEATURE:
<223> OTHER INFORMATION: GAPDH sense primer

<400> SEQUENCE: 5
tccaccaccc tgttgctgta g                                             21

<210> SEQ ID NO 6
<211> LENGTH: 19
```

```
<212> TYPE: DNA
<213> ORGANISM: Artificial Sequence
<220> FEATURE:
<223> OTHER INFORMATION: GAPDH antisense primer

<400> SEQUENCE: 6
gaccacagtc catgccatc                                               19
```